(12) United States Patent
Pisacane et al.

(10) Patent No.: US 11,571,718 B2
(45) Date of Patent: *Feb. 7, 2023

(54) CLEANING DEVICE WITH TAIL SWAB

(71) Applicant: Foamtec International Co., Ltd., Waco, TX (US)

(72) Inventors: Ferdinand Frederick Pisacane, San Diego, CA (US); Michael Strauss, Tamarac, FL (US)

(73) Assignee: Foamtec International Co., Ltd., Waco, TX (US)

(*) Notice: Subject to any disclaimer, the term of this patent is extended or adjusted under 35 U.S.C. 154(b) by 25 days.

This patent is subject to a terminal disclaimer.

(21) Appl. No.: 16/566,834

(22) Filed: Sep. 10, 2019

(65) Prior Publication Data
US 2020/0001330 A1    Jan. 2, 2020

Related U.S. Application Data (63) Continuation of application No. 15/135,236, filed on Apr. 21, 2016, which is a continuation of application No. 14/872,475, filed on Oct. 1, 2015.

(51) Int. Cl.
| | | |
|---|---|---|
| *B08B 1/00* | (2006.01) |
| *A61B 90/70* | (2016.01) |
| *B08B 9/043* | (2006.01) |
| *A61B 1/12* | (2006.01) |
| *A61B 17/00* | (2006.01) |

(52) U.S. Cl.
CPC .............. *B08B 1/003* (2013.01); *A61B 1/122* (2013.01); *A61B 90/70* (2016.02); *B08B 9/0436* (2013.01); *A61B 2017/00526* (2013.01); *A61B 2090/701* (2016.02)

(58) Field of Classification Search
None
See application file for complete search history.

(56) References Cited

U.S. PATENT DOCUMENTS

| | | | |
|---|---|---|---|
| 852,748 | A | 5/1907 | J. True. |
| 1,164,665 | A | 12/1915 | Reeves |
| 2,537,149 | A | 1/1951 | McKean |
| 3,205,518 | A | 9/1965 | Romaine |
| 3,591,885 | A | 7/1971 | Fritzen, Jr. |
| 3,708,820 | A | 1/1973 | Schultea |
| 4,114,224 | A | 9/1978 | Disko |
| 4,215,478 | A | 8/1980 | Thomas et al. |
| 4,497,082 | A | 2/1985 | Kogasaka |
| 4,499,625 | A | 2/1985 | Bottomley |
| 4,694,605 | A | 9/1987 | Garcia et al. |
| 5,735,808 | A | 4/1998 | Delgado et al. |
| 7,441,363 | B1 | 10/2008 | Black et al. |
| 8,176,592 | B1 | 5/2012 | Carpenter et al. |
| 8,651,116 | B2 | 2/2014 | Slack et al. |

(Continued)

FOREIGN PATENT DOCUMENTS

| | | |
|---|---|---|
| CA | 2842584 A1 | 8/2014 |
| WO | 2007013196 A1 | 2/2007 |

OTHER PUBLICATIONS

International Search Report and the Written Opinion of the International Searching Authority issued in application No. PCT/US2015/053792 dated Dec. 22, 2015.

*Primary Examiner* — Brian D Keller
(74) *Attorney, Agent, or Firm* — Zeman-Mullen & Ford LLP (57) ABSTRACT

A cleaning device with tail swab having a plurality of soft elongated strips.

18 Claims, 9 Drawing Sheets

(56) References Cited

U.S. PATENT DOCUMENTS

| | | |
|---|---|---|
| D800,981 S | 10/2017 | Pisacane et al. |
| 2004/0181194 A1 | 9/2004 | Perkins |
| 2010/0145143 A1 | 6/2010 | Salomon et al. |
| 2011/0289705 A1 | 12/2011 | Asano et al. |
| 2014/0228677 A1 | 8/2014 | Grudem, Jr. et al. |
| 2014/0237748 A1 | 8/2014 | Sweeney |
| 2014/0250614 A1 | 9/2014 | Pisacane |

CLEANING DEVICE WITH TAIL SWAB

CROSS-REFERENCE TO RELATED APPLICATIONS

This application is a continuation of and claims the benefit of, and priority to U.S. Nonprovisional patent application Ser. No. 15/135,236 filed Apr. 21, 2016, currently pending, which is a continuation application of U.S. Nonprovisional patent application Ser. No. 14/872,475 filed Oct. 1, 2015, currently pending, which applications are hereby incorporated by reference in its entireties.

FIELD OF INVENTION

The present invention generally relates to a cleaning device having an elongated tail swab that is especially useful for cleaning surgical instruments and medical devices. More particularly, the present invention relates to a cleaning device which includes an elongated flexible leader member, a tail swab having a plurality of soft elongated strips attached to one end of the leader member, and a polymer material covering at least a portion of the tail swab and the end of the leader member where the tail swab member is attached to the leader member.

BACKGROUND OF THE INVENTION

Medical devices and medical instruments are becoming more sophisticated and much smaller thereby enabling surgeons to reach remote parts of the body without the need for open surgery which exposes a much larger part of the body to the risk of outside infections. In addition, using these instruments results in lowering the complications of surgery and speeding up the recovery time for patients. However, these devices and instruments must be cleaned and decontaminated after use so that they can be reused in future procedures. This cleaning and decontamination process is often called reprocessing.

Reprocessing medical instruments and devices can become difficult with the newest and latest devices which often include miniscule channels and crevices that can be impossible to see and troublesome to access. In addition, the instruments and devices sometimes fail to come with adequate cleaning instructions or include cleaning instructions that are confusing and onerous to follow. As a result, many of these instruments and devices are reused without proper cleaning which can lead to severe risks for patients.

A University of Michigan study analyzed the cleanliness of 350 suction tips used to vacuum up fluids during surgery and found that 95 percent of them still contained debris after routine reprocessing. In another study, the Centers for Disease Control (CDC) conducted an investigation into seven individual, who contracted surgical-site bacterial infections after having knee or shoulder arthroscopy in a Houston hospital. The CDC found that the arthroscopic shavers that were used for the procedures contained residual bits of body tissue. Endoscopes and cannulas are even more worrisome to infectious disease experts in that millions of surgical procedures are performed each year using these instruments.

Surgical instruments like endoscopes and cannulas are typically cleaned with twisted metal wire brushes and pipe cleaning type devices. However, these types of cleaning devices can cause major problems including incomplete cleaning, damage to medical devices and instruments resulting from scratching, and metal fibers and other types of cleaning fibers left inside the instruments after cleaning. In addition, these types of cleaning devices are high in cost to produce and therefore need to be reused, thereby carrying the attendant risks of cross contamination.

Accordingly, there is a need for a simple, low cost cleaning device which overcomes these obstacles. There is also a particular need for a simple, low cost device specifically designed for cleaning medical instruments and medical devices such as endoscopes and cannulas without the risk of damaging the instruments and further risking infection to patients.

SUMMARY OF THE INVENTION

The present invention is directed to a cleaning device with a tail swab having a plurality of soft elongated strips. In one exemplary embodiment, the cleaning device with tail swab includes a flexible leader member having a first end and a second end, a tail swab having a plurality of soft elongated strips attached to the second end of the leader member where the plurality of soft elongated strips are shorter in length than the leader member, and a polymer material covering at least a portion of the tail swab and the second end of the leader member. A separate polymer material may also cover the first end of the leader member and this polymer material may be comprised of the same polymer material that covers the second end of the leader member and at least a portion of the tail swab.

One exemplary embodiment of the tail swab includes a single strip of soft material that is cut at opposite ends to form a plurality of soft elongated strips which are separated by a continuous middle portion of the single strip of soft material. The width of the continuous middle portion of the single strip of soft material may be smaller than the width of each of the plurality of soft elongated strips and the length of the continuous middle portion of the single strip of soft material may be smaller than the length of each of the plurality of soft elongated strips. In another exemplary embodiment of the cleaning device with tail swab, the leader member is at least one meter in length and the plurality of elongated strips are at least 100 millimeters in length.

The second end of the leader member that is attached to the tail swab may be folded to form a hook like member and the continuous middle portion of the single strip of soft material may be positioned within the hook like member. The leader member may comprise a wire coated with a polymer and the tail swab may comprise a foam material and/or a microfiber material. The polymer material that covers at least a portion of the tail swab and the second end of the leader member may be a heat shrink polymer tube member and a separate heat shrink polymer tube member may also be used as the polymer that covers the first end of the leader member.

In still another exemplary embodiment of the cleaning device with tail swab, the cleaning device includes an elongated leader member having opposite ends where the leader member is at least one meter in length and a tail swab having a plurality of soft elongated strips that are shorter in length than the leader member where the tail swab is attached to an end of the leader member. A polymer material may cover at least a portion of the tail swab and the end of the leader member where the tail swab is attached as well as the end of the leader member opposite where the tail member is attached. The tail swab may comprise a single soft strip that is cut to form a plurality of soft elongated strips that are separated by a continuous middle portion of the single soft strip. The width of the continuous middle portion of the single soft strip may be smaller than the width of each of the plurality of soft elongated strips and the length of the continuous middle portion of the soft single strip may be smaller than the length of each of the plurality of soft elongated strips.

The end of the leader member where the tail member is attached may comprise a hook like shape or hook member where the continuous middle portion of the single soft strip is positioned within the hook member. The leader member may comprise a wire coated with a polymer and the tail swab may comprise a foam material and/or a microfiber material.

The present invention is also directed to a method for making a cleaning device with tail swab. In one exemplary embodiment, the method for making the cleaning device with tail swab includes the steps of providing an elongated leader member having opposite ends and folding one end of the leader member so it forms a hook like shape, cutting a single elongated strip of material to form a plurality of soft elongated strips separated by a continuous middle portion, positioning the continuous middle portion of the single elongated strip within the hook like shape of the leader member, and coating at least a portion of the continuous middle portion of the single elongated strip and the hook like shape at the end of the leader member with a polymer.

BRIEF DESCRIPTION OF THE DRAWINGS

The subject invention will hereinafter be described in conjunction with the appended drawing figures, wherein like numerals denote like elements.

DETAILED DESCRIPTION OF EXEMPLARY EMBODIMENTS

Figure 1:
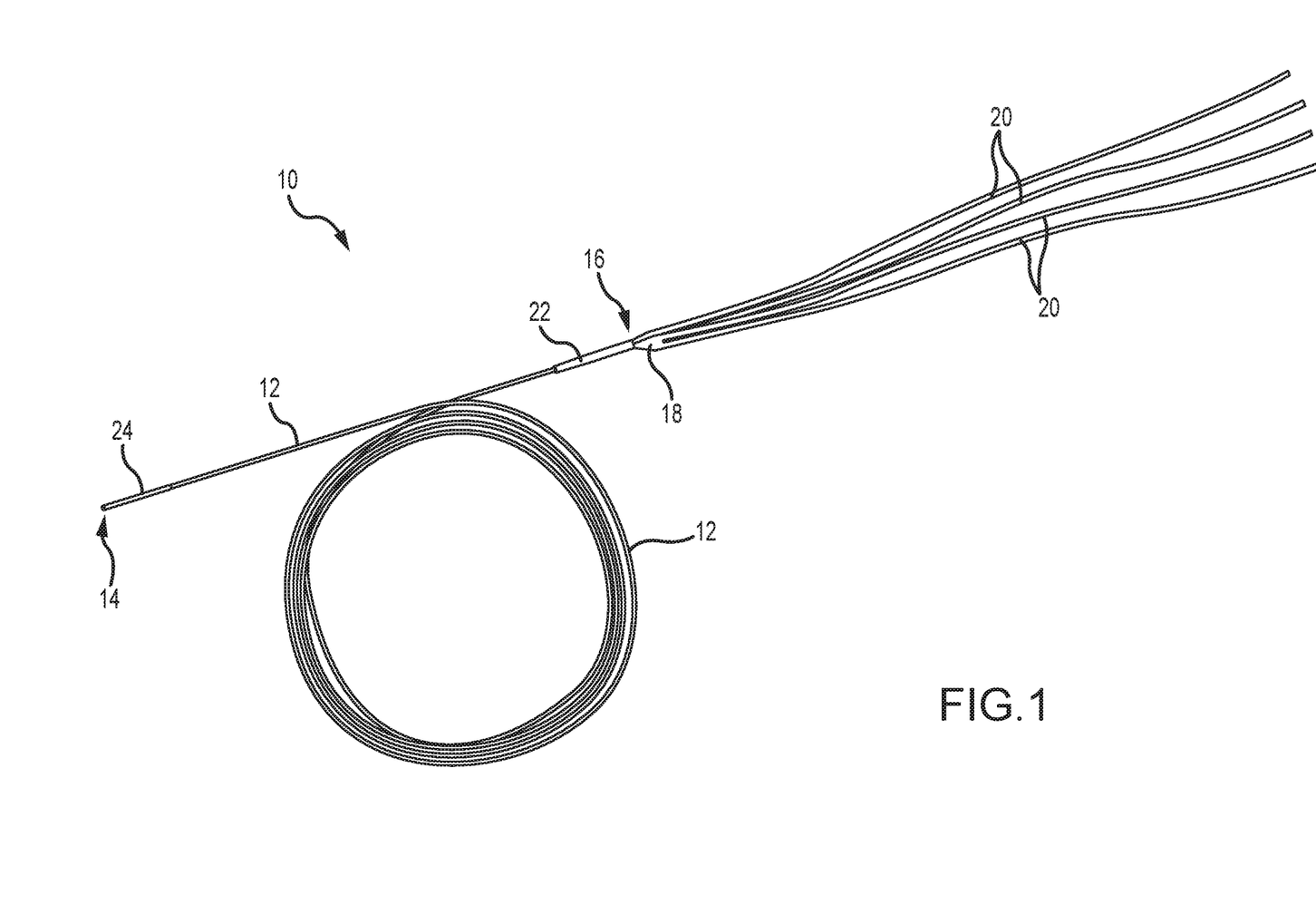
FIG. 1 is a perspective view of one exemplary embodiment of the cleaning device with tail swab of the present invention.

The cleaning device with tail swab of the present invention generally provides a flexible leader member and a tail swab having a plurality of soft elongated strips attached to an end of the leader member. FIG. 1 is a perspective view of one exemplary embodiment of the cleaning device 10 with tail swab of the present invention. Cleaning device 10 with tail swab includes an elongated flexible leader member 12 having a first end 14 and a second end 16, a tail swab 18 having a plurality of soft elongated strips 20 attached to the second end 16 of the elongated flexible leader member 12, and a polymer material 22 covering at least a portion of the tail swab 18 and the second end 16 of the elongated flexible leader member 12. A separate polymer material 24 may cover the first end 14 of the elongated flexible leader member 12 to enable the first end 14 to be inserted into and pushed through a medical device or surgical instrument without scratching or damaging the interior of the medical device or surgical instrument. Once the first end 14 is pushed through and to the outside of a medical device or surgical instrument, the cleaning device 10 with tail swab can be pulled through the interior of the medical device or surgical instrument by pulling on first end 14 thereby enabling the length of the elongated flexible leader member 12 and the tail swab 18, including its plurality of soft elongated strips 20, to be pulled through the medical device or surgical instrument to clean the interior of the medical device or surgical instrument. The plurality of soft elongated strips 20 of tail swab 18 enable effective, efficient and non-abrasive cleaning of the interior of any medical device or surgical instrument that contains a channel or channels that are inaccessible for cleaning.

Leader member 12 may be comprised of any flexible material that has reduced potential for contamination. For example, leader member 12 may be comprised of a flexible metal covered with a polymer material. One such non-limiting example is a leader member comprising a stainless steel wire coated with a nylon material. Leader member 12 may comprise a rod-like shape and all or a portion of leader member 12 may be colored to effect color coding of different embodiments of the cleaning device 10 with tail swab, namely embodiments with different leader member lengths, embodiments with different tail swab lengths, and embodiments with different tail swab configurations. Tail swab 18 may be comprised of any type of soft absorbent material such as, but not limited to, a foam material and/or a cloth type material. One particularly effective material for tail swab 18 is a continuous filament micro denier, soft polyester/nylon textile woven from an abrasion resistant fabric. It may also have a non-symmetrical micro fiber structure. The polymer material 22 and separate polymer material 24 may each comprise a heat shrink polymer tube that can be easily placed over flexible leader member 12 and then heated to conform to the shape of the end of the leader member and/or the shape of the tail swab that is covered by the polymer material to form a good mechanical connection that is adhesive free. In addition, instead of a heat shrink polymer tube, the polymer material may comprise an elastomeric material that can be over molded on top of the leader member 12, ends 14, 16 of the leader member 12, and/or tail swab 18 to form a good, non-adhesive, mechanical connection.

Figure 2:
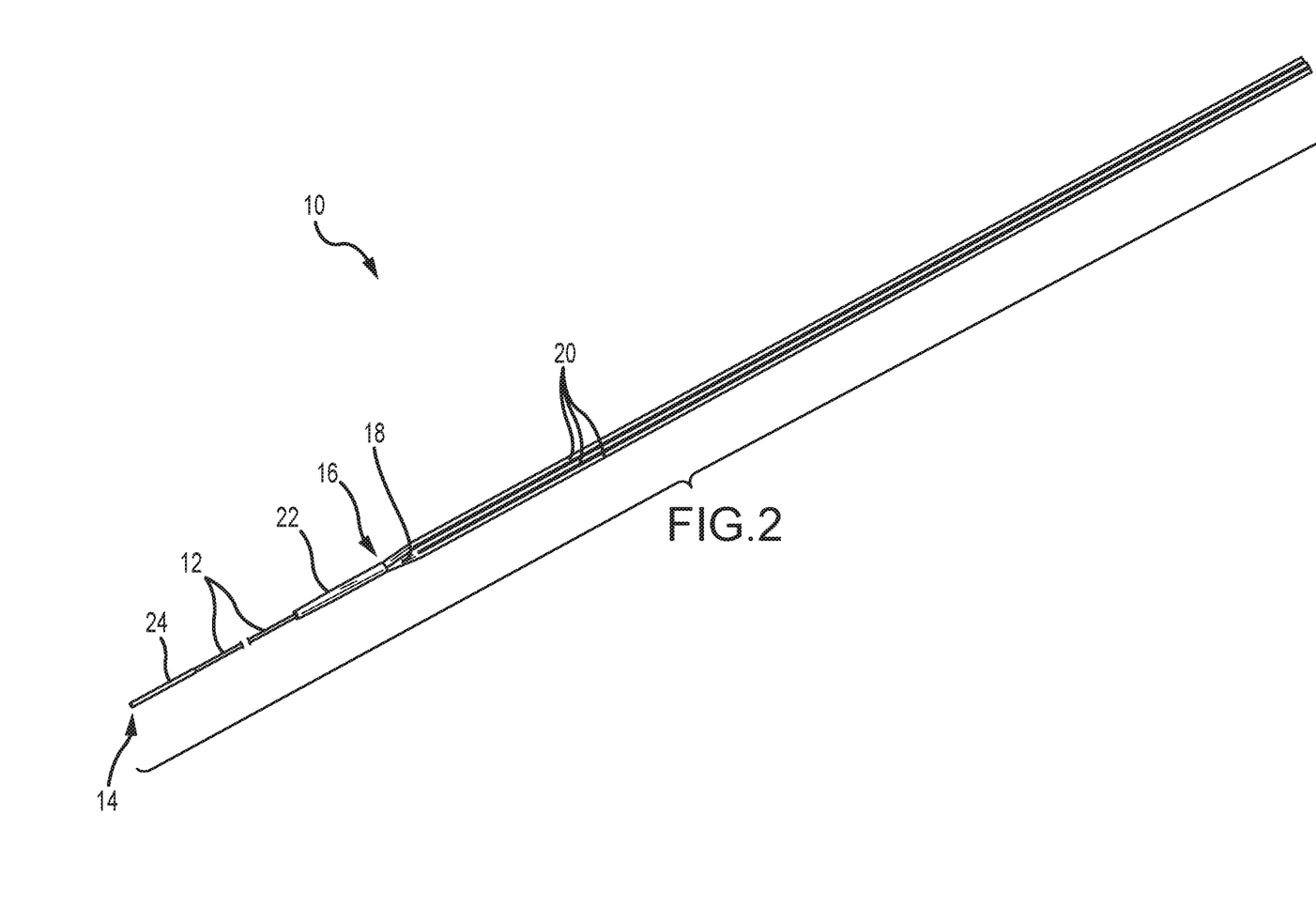
FIG. 2 is a top perspective view of the exemplary embodiment of the cleaning device with tail swab shown in FIG. 1 with the flexible leader member and tail swab both shown extended to a straight position.

FIG. 2 is a top perspective view of the exemplary embodiment of the cleaning device 10 with tail swab shown in FIG. 1 with the flexible leader member 12 and tail swab 18 both shown extended to a straight position. The length of the tail swab 18 and the plurality of soft elongated strips 20 of tail swab 18 are shorter than the length of the flexible leader member 12. The leader member 12 may have any length that is longer than the tail swab 18 and that is also long enough to be pushed through a channel or interior of a medical device or surgical instrument so that its opposite ends can remain outside the medical device or surgical instrument after one of its ends has been pushed through the medical device or surgical instrument. One particularly useful length for the flexible leader member 12 is a length that is at least one meter. Another exemplary embodiment of the cleaning device 10 with tail swab may have a flexible leader member that is at least two meters in length depending on the device or instrument to be cleaned.

Figure 3:
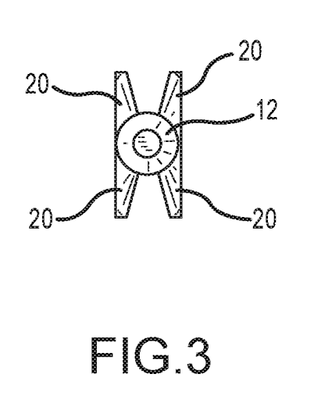
FIG. 3 is a front elevational view of the exemplary embodiment of the cleaning device with tail swab shown in FIG. 2.
Figure 4:
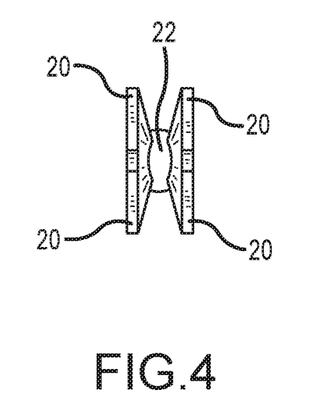
FIG. 4 is a rear elevational view of the exemplary embodiment of the cleaning device with tail swab shown in FIG. 2.

FIG. 3 is a front elevational view of the exemplary embodiment of the cleaning device 10 with tail swab shown in FIG. 2 and FIG. 4 is a rear elevational view of the exemplary embodiment of the cleaning device 10 with tail swab shown in FIG. 2. As can be seen in FIGS. 3 and 4, the width of each of the plurality of soft elongated strips 20 of tail swab 18 may be larger than the diameter of the flexible leader member 12.

Figure 5:
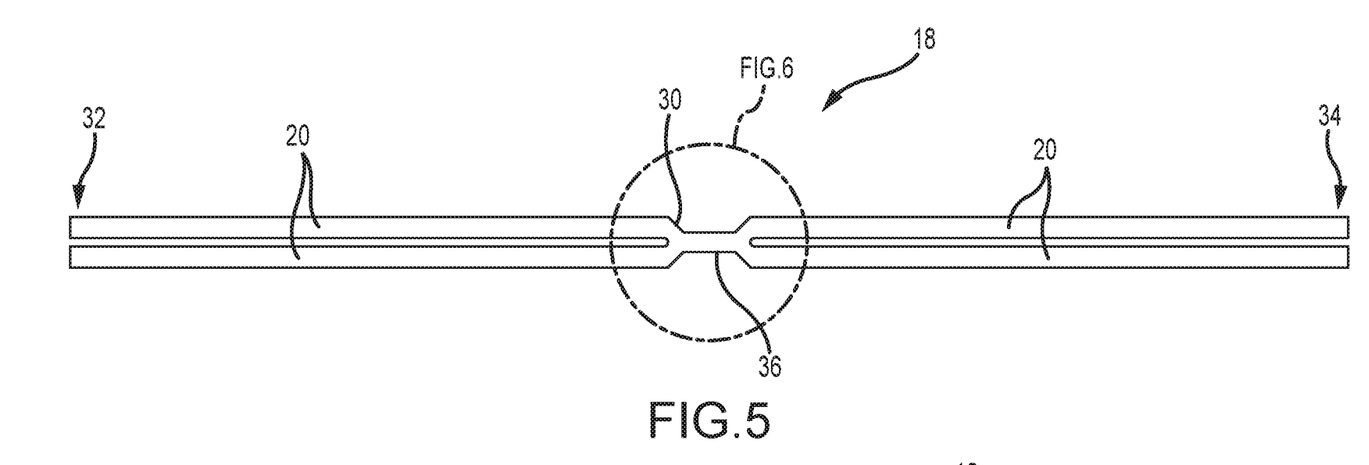
FIG. 5 is a top plan view of an exemplary embodiment of the tail swab of the cleaning device with tail swab of the present invention.

A top plan view of an exemplary embodiment of the tail swab 18 of the cleaning device 10 with tail swab of the present invention is shown in FIG. 5. In this exemplary embodiment, tail swab 18 is made from a single strip 30 of a soft material that is cut at opposite ends 32, 34 of the single strip 30 to form the plurality of soft elongated strips 20 which are separated by a continuous middle portion 36 of single strip 30. It will be understood by those skilled in the art that the opposite ends 32, 34 of single strip 30 may be cut inward from their opposite ends to form any number and length of the plurality of soft elongated strips 20. It will also be understood by those skilled in the art that single strip 30 may start out as a strip of material having a continuous length and width that is later machine cut to form the plurality of soft elongated strips 20 and the continuous middle portion 36 so that the continuous middle portion 36 has a smaller width than each of the plurality of soft elongated strips 20. Moreover, single strip 30 may not be cut at all and may simply be used to form two soft elongated strips 20 of tail swab 18 by connecting the middle of the single strip 30 to an end of leader member 12 or by folding single strip 30 in half and connecting the folded portion of the single strip 30 to an end of leader member 12. It will also be understood by those skilled in the art that, although not as potentially contaminate free and/or particle free, another method may be used to create the plurality of soft elongated strips 20, namely separately cutting and/or forming a plurality of soft strips 20 and then attaching an end of each of those strips 20 to an end of leader member 12 one exemplary embodiment of the plurality of soft elongated strip members 20, the length of the plurality of soft elongated strip members 20 in any of the exemplary embodiments of the tail swab 18 may be at least 100 millimeters long. In another exemplary embodiment of the plurality of soft elongated strip members 20, the length of the plurality of soft elongated strip members 20 in any of the exemplary embodiments of the tail swab 18 may be at least 200 millimeters long.

Figure 6:
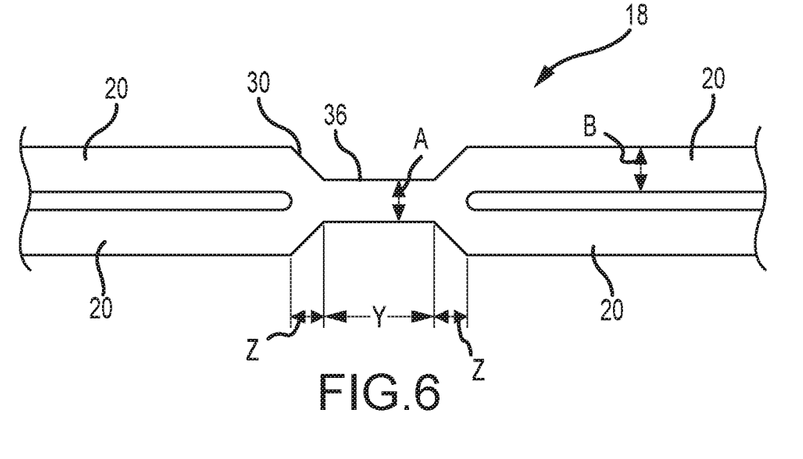
FIG. 6 is a magnified view of a portion of the exemplary embodiment of the tail swab shown in FIG. 5.

FIG. 6 is a magnified view of a portion of the exemplary embodiment of the tail swab 18 shown in FIG. 5. As can be seen from this exemplary embodiment, width A of continuous middle portion 36 of single strip 30 is smaller than width B of each of the plurality of soft elongated strips 20 of single strip 30. In one exemplary embodiment width A is 2.5 millimeters and width B is 5.0 millimeters. Length Y of continuous middle portion 36 of single strip 30 may be equal to, less than, or greater than length Z which is the length from the end of continuous middle portion 36 of single strip 20 to the beginning of each separate plurality of elongated strips 20. In one exemplary embodiment length Y may be 10 millimeters and length Z may be 10 millimeters. In another exemplary embodiment, length Y may be 10 millimeters and length Z may be 20 millimeters.

Figure 7:
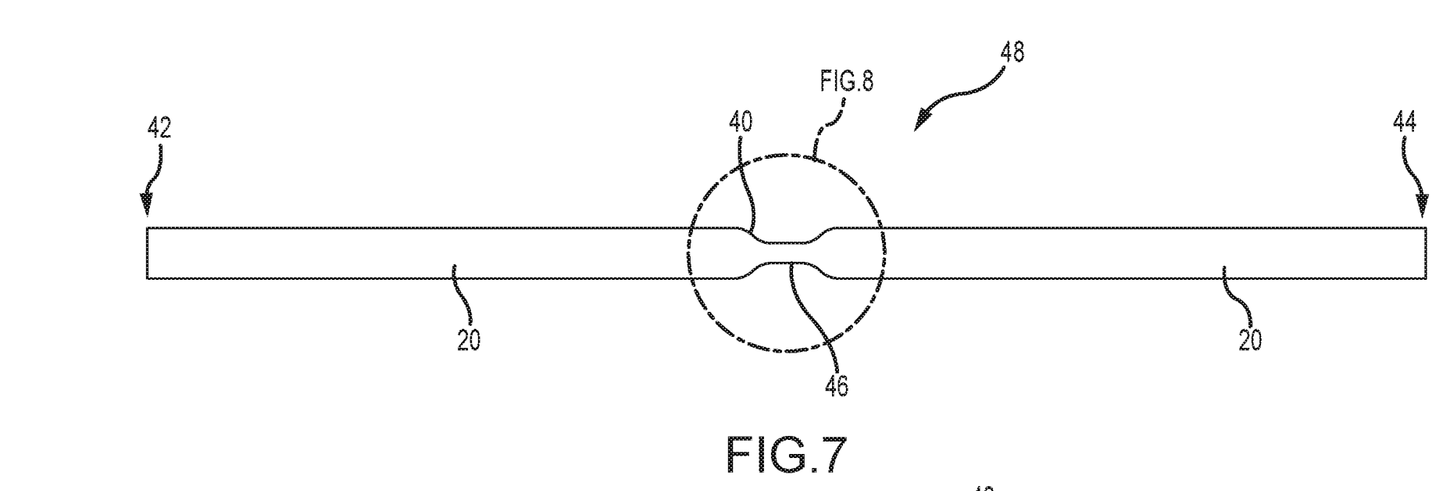
FIG. 7 is a top plan view of another exemplary embodiment of the tail swab of the cleaning device with tail swab of the present invention.

A top plan view of another exemplary embodiment of the tail swab 48 of the cleaning device 10 with tail swab of the present invention is shown in FIG. 7. In this exemplary embodiment, tail swab 48 is made from a single strip 40 of a soft material that is cut in the middle to form the plurality of soft elongated strips 20 which are separated by a continuous middle portion 46 of single strip 40. The continuous middle portion 46 has a smaller width than each of the plurality of soft elongated strips 20. Moreover, in a different exemplary embodiment, single strip 30 may not be cut at all and may simply be used to form two soft elongated strips 20 of tail swab 48 by connecting the middle of the single strip 40 to an end of leader member 12 or by folding single strip 40 in half and connecting the folded portion of the single strip 40 to an end of leader member 12. In this different embodiment, the continuous middle portion 46 would have a width equal to the width of each of the plurality of soft elongated strips 20. It will also be understood by those skilled in the art that, although not as potentially contaminate free and/or particle free, another method may be used to create the plurality of soft elongated strips 20, namely separately cutting and/or forming a plurality of soft strips 20 and then attaching an end of each of those strips 20 to an end of leader member 12. As previously mentioned above, in one exemplary embodiment of the plurality of soft elongated strip members 20, the length the plurality of soft elongated strip members 20 in any of the exemplary embodiments of the tail swab 18 may be at least 100 millimeters long. Further, as previously mentioned above, in another exemplary embodiment of the plurality of soft elongated strip members 20, the length of the plurality of soft elongated strip members 20 in any of the exemplary embodiments of the tail swab 18 may be at least 200 millimeters long.

Figure 8:
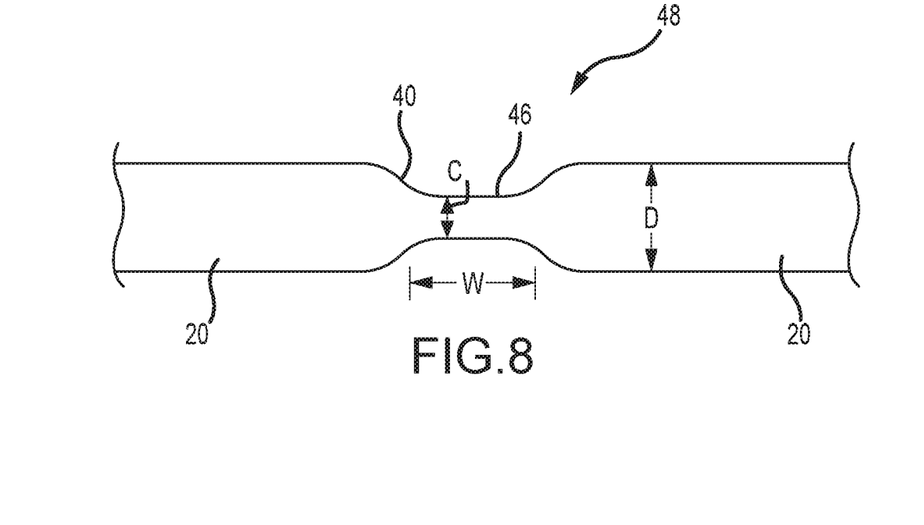
FIG. 8 is a magnified view of a portion of the exemplary embodiment of the tail swab shown in FIG. 7.

FIG. 8 is a magnified view of a portion of the exemplary embodiment of the tail swab 48 shown in FIG. 7. As can be seen from this exemplary embodiment, width C of continuous middle portion 46 of single strip 40 is smaller than width D of each of the plurality of soft elongated strips 20 of single strip 40. In one exemplary embodiment width A may be 2.5 millimeters and width B may be 3.0 millimeters. Length Y of continuous middle portion 46 of single strip 30 may be 10 millimeters.

Figure 9:
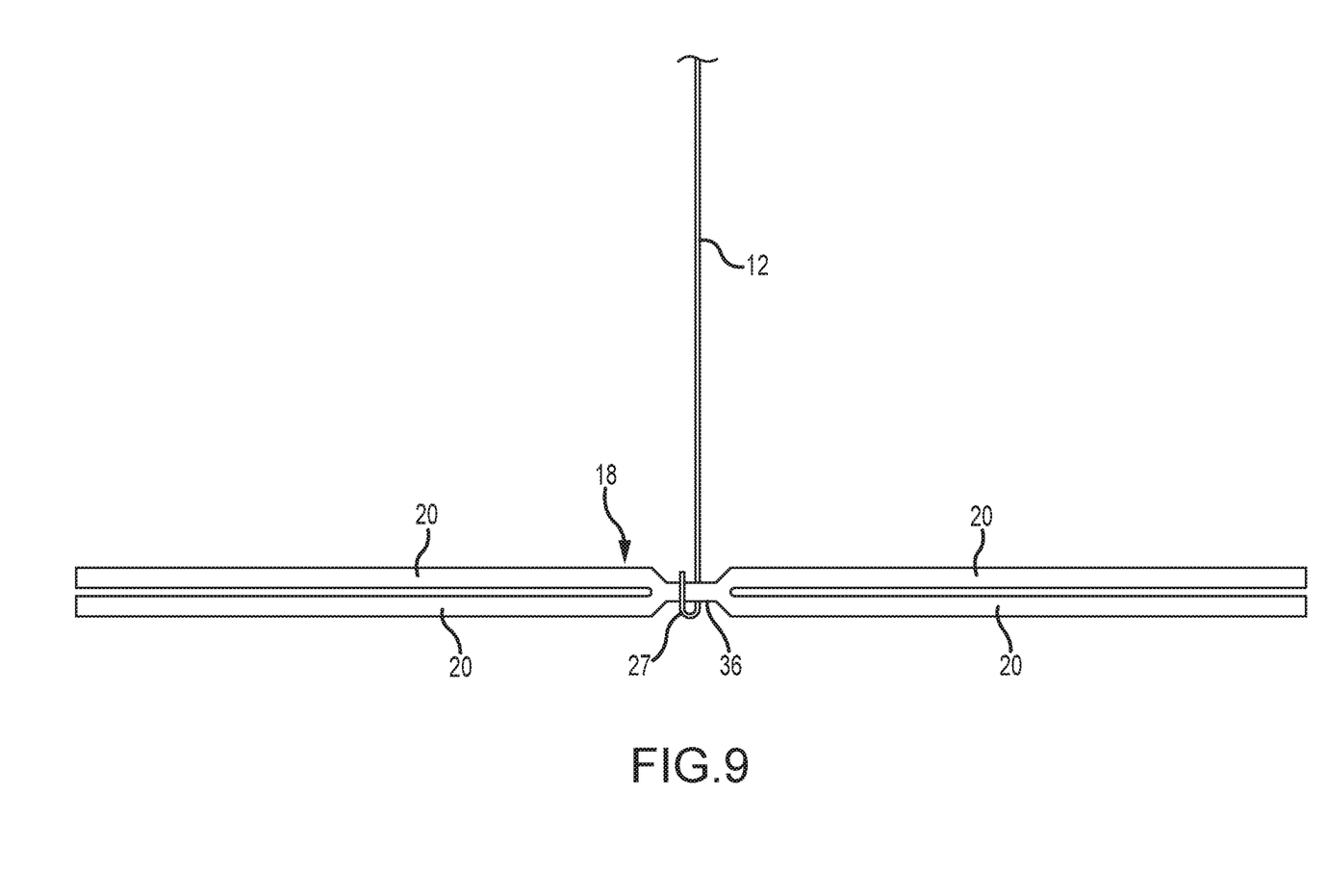
FIG. 9 is a top plan view showing attachment of the tail swab shown in FIG. 5 to a leader member of the cleaning device with tail swab of the present invention.
Figure 10:
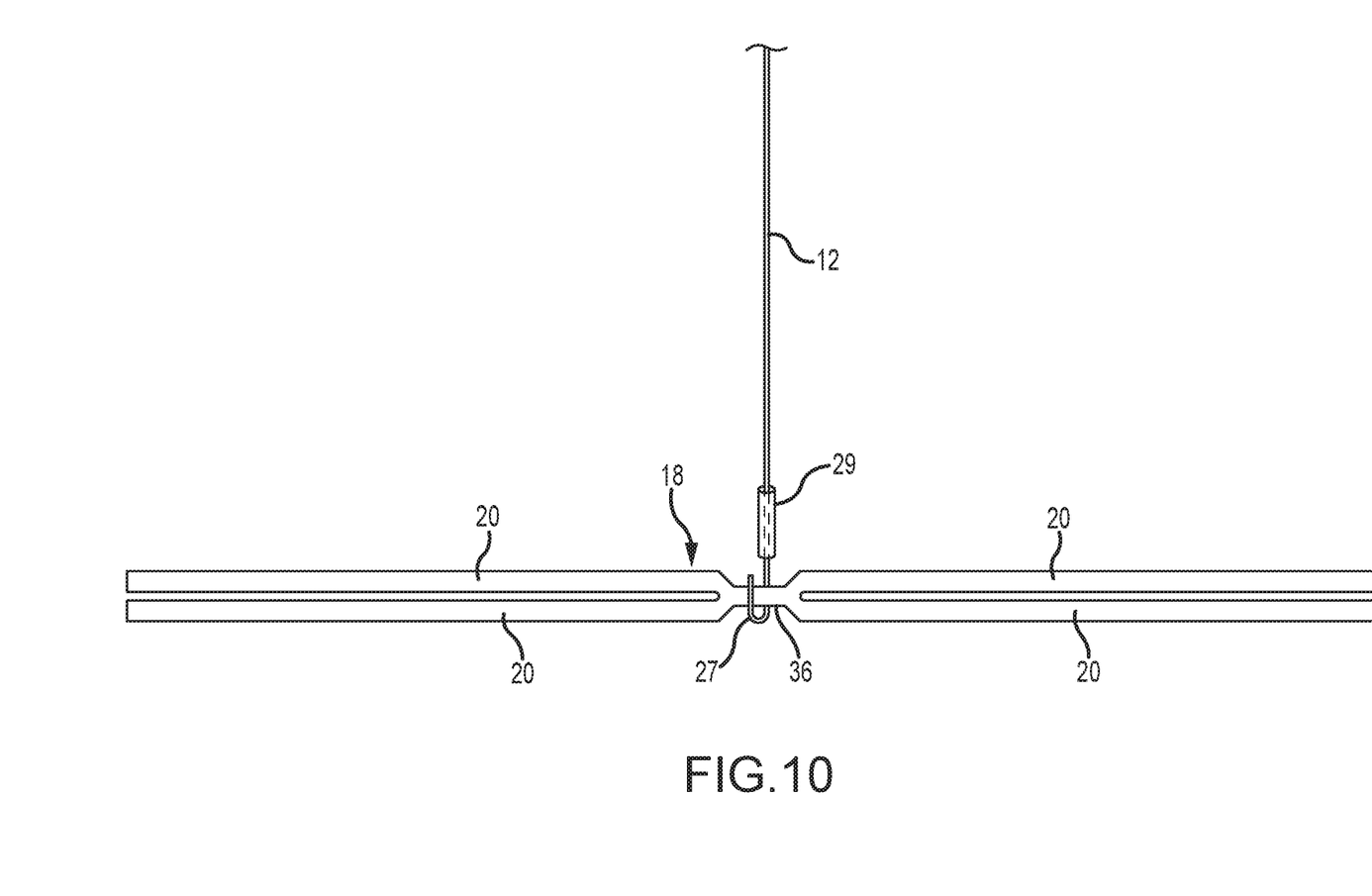
FIG. 10 is the top plan view shown in FIG. 9 with the addition of a polymer shrink tube member placed over the leader member.

FIG. 9 is a top plan view showing attachment of the tail swab 18 shown in FIG. 5 to a leader member 12 of the cleaning device with tail swab of the present invention and FIG. 10 is the top plan view shown in FIG. 9 with the addition of a polymer material 22 in the form of a polymer shrink tube member placed over the leader member 12. Flexible leader member 12 has a first end (not shown) and a second end 16. Second end 16 of leader member 12 is folded or bent to form a hook like shape or hook like member 27, Continuous middle portion 36 of the single strip 30 of tail member 18 is positioned within the hook like member 27. A polymer material 22 such as polymer shrink tube member 29 is placed on leader member 12 by inserting lead member 12 through the polymer shrink tube member 29 as shown in FIG. 10. After the continuous middle portion 36 of the single strip 30 of tail member 18 is positioned within the hook like member 27, the polymer shrink tube member 29 is slid down over the hook like member 27 and the continuous middle portion 36 thereby pushing the plurality of soft elongated strips 20 in a direction away from leader member 12. The polymer shrink tube member 9 can then be heated to form a good, non-adhesive, mechanical connection of the tail swab 18 to the leader member 12. It will also be understood by those skilled in the art that, instead of a heat shrink polymer tube, the polymer material 22 and separate polymer material 24 may comprise an elastomeric material that can be over molded on top of the leader member 12, ends 14, 16 of the leader member 12, and/or tail swab 18 to form a good, non-adhesive, mechanical connection.

Figure 11:
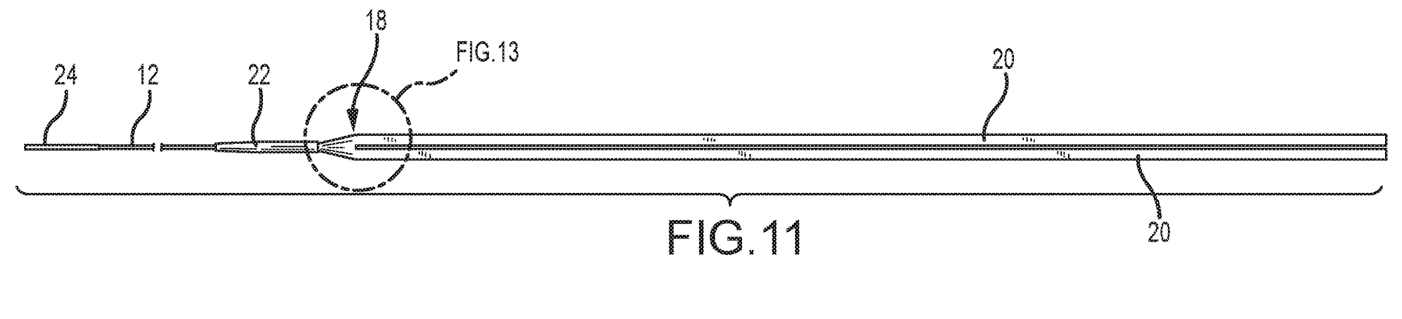
FIG. 11 is a side elevational view of the exemplary embodiment of the cleaning device with tail swab shown in FIG. 2.
Figure 12:
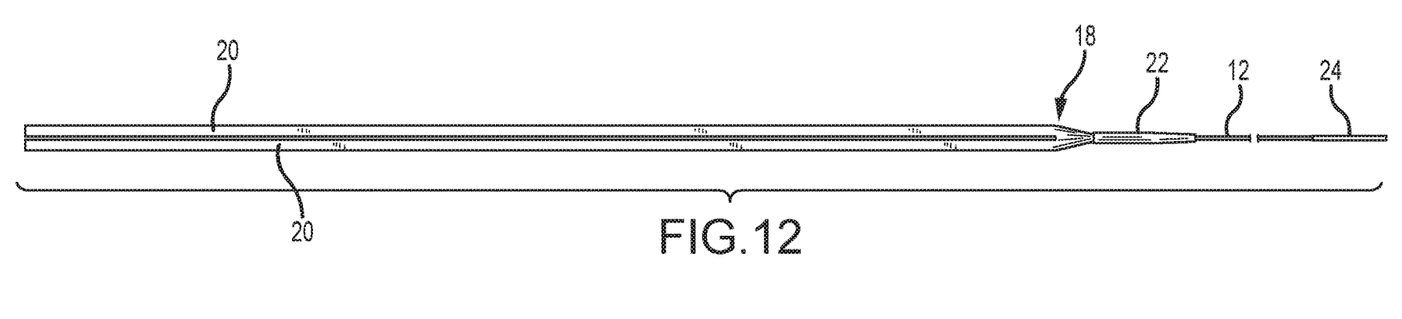
FIG. 12 is an opposite side elevational view of the cleaning device with tail swab shown in FIG. 2.
Figure 13:
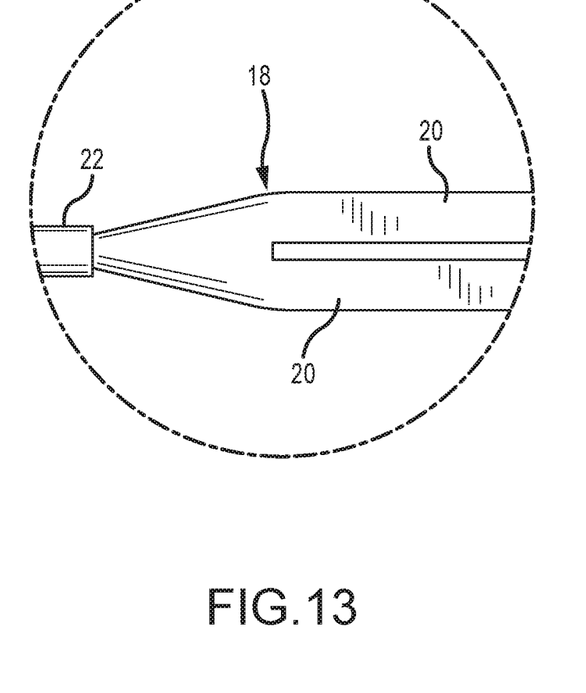
FIG. 13 is a magnified view of a portion of the exemplary embodiment of the cleaning device with tail swab shown in FIG. 11.

FIG. 11 is a side elevational view of the exemplary embodiment of the cleaning device 10 with tail swab shown in FIG. 2 and FIG. 12 is an opposite side elevational view of the cleaning device 10 with tail swab shown in FIG. 2. FIG. 13 is a magnified view of a portion of the exemplary embodiment of the cleaning device 10 with tail swab shown in FIG. 11 that clearly shows the non-adhesive, mechanical connection of the lead member 12 to the tail swab 18 having a plurality of soft elongated strips 20 by way of using the polymer material 22, exemplary embodiments of which have been previously described above.

The present invention is also directed to a method for making a cleaning device with tail swab. In one exemplary embodiment, the method for making the cleaning device with tail swab includes the steps of providing an elongated leader member having opposite ends and folding one end of the leader member so it forms a hook like shape, cutting a single elongated strip of material to form a plurality of soft elongated strips separated by a continuous middle portion, positioning the continuous middle portion of the single elongated strip within the hook like shape of the leader member, and coating at least a portion of the continuous middle portion of the single elongated strip and the hook like shape at the end of the leader member with a polymer. The method may also include covering the end of the leader member opposite the hook like shape end of the leader member with a separate polymer material.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A cleaning device with tail swab comprising:
   an elongated flexible leader member having a first end and a second end; and
   a tail swab comprising a single continuous strip that is cut to form a plurality of strips that extend from opposite sides of a continuous middle portion of the single continuous strip wherein the continuous middle portion extends from near an end of the plurality of strips located at one side of the single continuous strip to near an end of the plurality of strips located at the opposite side of the single continuous strip wherein a width of the continuous middle portion of the single continuous strip is smaller than a width of each of the plurality of strips and wherein the plurality of strips are longer in length than the continuous middle portion of the single continuous strip and the tail swab is attached to the second end of the leader member.

2. The cleaning device of claim 1 further comprising a polymer material covering at least a portion of the tail swab and the second end of the leader member.

3. The cleaning device of claim 2 wherein the polymer material comprises a heat shrink polymer tube member.

4. The cleaning device of claim 2 wherein a separate polymer material also covers the first end of the leader member.

5. The cleaning device of claim 1 wherein the single continuous strip is cut at opposite ends to form the plurality of strips which are separated by the continuous middle portion of the single continuous strip.

6. The device of claim 1 wherein the second end of the leader member comprises a hook member and the continuous middle portion of the single continuous strip of the tail swab is positioned within the hook member of the leader member.

7. The cleaning device of claim 1 wherein the leader member comprises a wire coated with a polymer.

8. The cleaning device of claim 1 wherein the tail swab comprises at least one of a foam material and/or a microfiber material.

9. The cleaning device of claim 1 wherein the plurality of strips are at least 100 millimeters in length.

10. The cleaning device of claim 1 wherein the elongated leader member is at least one meter in length.

11. A cleaning device with tail swab comprising:
    an elongated flexible leader member having a first end and a second end wherein the second end of the leader member comprises a hook member;
    a tail swab comprising a single continuous strip that is cut to form a plurality of strips that extend from opposite sides of a continuous middle portion of the single continuous strip wherein the continuous middle portion extends from near and end of the plurality of strips located at one side of the single continuous strip to near an end of the plurality of strips located at the opposite side of the single continuous strip and wherein the continuous middle portion of the single continuous strip is positioned within the hook member of the leader member; and a polymer material covering at least a portion of the tail swab and the second end of the leader member.

12. The cleaning device of claim 11 wherein the polymer material comprises a heat shrink polymer tube member.

13. The cleaning device of claim 11 wherein a separate polymer material also covers the first end of the leader member.

14. The cleaning device of claim 11 wherein a width of the continuous middle portion of the single continuous strip is smaller than a width of each of the plurality of strips.

15. The cleaning device of claim 11 wherein the leader member comprises a wire coated with a polymer.

16. The cleaning device of claim 11 wherein the tail swab comprises at least one of a foam material and/or a microfiber material.

17. The cleaning device of claim 11 wherein the plurality of strips are at least 100 millimeters in length.

18. The cleaning device of claim 11 wherein the elongated leader member is at least one meter in length.

* * * * *